United States Patent [19]

Lopez

[11] Patent Number: 5,258,361
[45] Date of Patent: Nov. 2, 1993

[54] HERBICIDAL 1-(DISUBSTITUTED CARBAMOYL)-3-(N-ARYLSULFONAMIDO)-1,2,4-TRIAZOLES

[75] Inventor: Raul C. G. Lopez, Doylestown, Pa.

[73] Assignee: Rohm and Haas Company, Philadelphia, Pa.

[21] Appl. No.: 768,132

[22] Filed: Sep. 27, 1991

[51] Int. Cl.$^5$ ............... A01N 43/653; C07D 249/12
[52] U.S. Cl. ................... 504/273; 504/249; 546/210; 548/263.2
[58] Field of Search .......... 548/263.2; 71/92; 546/210; 504/249, 273

[56]         References Cited
        U.S. PATENT DOCUMENTS

| | | | |
|---|---|---|---|
| 3,308,131 | 3/1967 | McKusick | 546/210 |
| 4,148,626 | 4/1979 | Brookes et al. | 71/92 |
| 4,280,831 | 7/1981 | Patel | 71/92 |
| 4,810,271 | 3/1989 | Nakayama et al. | 71/92 |

OTHER PUBLICATIONS

Derwent Alerting Abstracts Bulletin, Chemical Patents Index, Number 84-092381/15 of Japanese Patent 59-39880, dated Mar. 1984.

Primary Examiner—Patricia L. Morris
Attorney, Agent, or Firm—Clark R. Carpenter

[57] ABSTRACT

This invention relates to 1-(disubstituted carbamoyl)-3-(N-arylsulfonamido)-1,2,4-triazoles of the formula

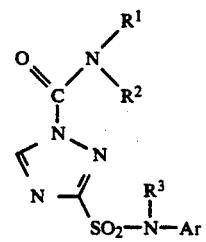

wherein $R^1$ and $R^2$ are each independently selected from the group consisting of alkyl, alkenyl, alkynyl, cycloalkyl, cycloalkylalkyl, cycloalkenyl, cycloalkenylalkyl, haloalkyl, alkoxyalkyl and haloalkoxyalkyl, $R^3$ is hydrogen, alkyl, alkenyl, alkynyl, cycloalkyl, cycloalkylalkyl, cycloalkenyl, cycloalkenylalkyl, haloalkyl, alkoxyalkyl or haloalkoxyalkyl, Ar is an optionally substituted aryl group, and the agronomically acceptable acid addition salts and metal complexes thereof, compositions containing these compounds and their uses as herbicides.

14 Claims, No Drawings

HERBICIDAL 1-(DISUBSTITUTED CARBAMOYL)-3-(N-ARYLSULFONAMIDO)-1,2,4-TRIAZOLES

FIELD OF THE INVENTION

This invention relates to 1-(disubstituted carbamoyl)-3-(N-arylsulfonamido)-1,2,4-triazoles, their acid addition salts and metal complexes, compositions containing these compounds, and the use of these compounds as herbicides.

BACKGROUND OF THE INVENTION

Chemical weed control agents enable more efficient crop production by elimination of competing plant growth. During the past years, there has been an intensified search for herbicides to control unwanted plants.

A number of carbamoyl substituted triazoles are known to be useful as herbicides. For example, Nakayama, et al., U.S. Pat. No. 4,810,271 disclose dialkylcarbamoyl triazoles substituted by alkyl-sulfonyl, -sulfinyl and -thio groups as herbicides. No sulfonamido substituted triazoles are disclosed. Brooks, et al., U.S. Pat. No. 4,148,626 disclose as herbicides a broad group of 1-disubstitutedcarbamoyl-3-substituted triazoles including 3-alkylthio, alkylsulphinyl, alkylsulphonyl alkenylthio and disubstituted 3-sulfonamides. Patel, U.S. Pat. No. 4,280,831, discloses as a herbicide the single compound 3-benzylsulfonyl-1-diethylcarbamoyl-1,2,4-triazole. McKusick, U.S. Pat. No. 3,308,131, discloses as insecticides a broad group of 1-carbamoyl-3-substituted-1,2,4-triazoles. No sulfonamido substituted triazoles are disclosed. Derwent Alerting Abstracts Bulletin, Chemical Patents Index, Number 84-092381/15 of Japanese Patent 59-39880 discloses as herbicides a broad group of 1-carbamoyl-3-(substituted benzyl-sulfonyl, -sulfinyl and -thio)-1,2,4-triazoles. No sulfonamido substituted triazoles are disclosed. Thus, none of this art suggest the specific class of sulfonamido substituted triazoles of the present invention.

SUMMARY OF THE INVENTION

This invention relates to 1-(disubstituted carbamoyl)-3-(N-arylsulfonamido)-1,2,4-triazoles of the formula

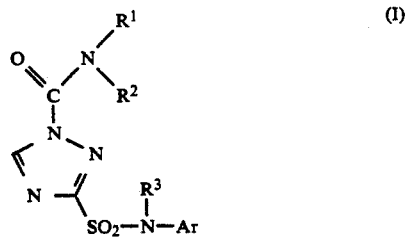

wherein:

$R^1$ and $R^2$ are each independently selected from the group consisting of alkyl, alkenyl, alkynyl, cycloalkyl, cycloalkylalkyl, cycloalkenyl, cycloalkenylalkyl, haloalkyl, alkoxyalkyl and haloalkoxyalkyl, or $R^1$ and $R^2$ may together represent a $(C_4-C_5)$alkylene group or a $(C_4-C_5)$alkylene group substituted with up to two substituents each independently selected from the group consisting of alkyl, alkenyl, alkynyl, halo, haloalkyl, alkoxyalkyl and haloalkoxyalkyl so as to form a nitrogen-containing five or six membered cyclic ring with the nitrogen to which they attach, $R^3$ is hydrogen, alkyl, alkenyl, alkynyl, cycloalkyl, cycloalkylalkyl, cycloalkenyl, cycloalkenylalkyl, haloalkyl, alkoxyalkyl or haloalkoxyalkyl, Ar is an aryl group or an aryl group substituted with up to three substituents each independently selected from the group consisting of alkyl, alkenyl, alkynyl, haloalkyl, alkoxy, haloalkoxy, alkoxyalkyl, haloalkoxyalkyl, cyano, nitro, alkoxycarbonyl and alkylthio, and the agronomically acceptable acid addition salts and metal complexes thereof, compositions containing these compounds and their uses as herbicides.

DETAILED DESCRIPTION OF THE INVENTION

This invention relates to compounds of the general formula (I) wherein:

$R^1$ and $R^2$ are each independently selected from the group consisting of $(C_1-C_6)$alkyl, $(C_3-C_4)$alkenyl, $(C_3-C_4)$alkynyl, $(C_3-C_6)$cycloalkyl, $(C_3-C_6)$cycloalkyl$(C_1-C_2)$alkyl, $(C_5-C_6)$cycloalkenyl, $(C_5-C_6)$cycloalkenyl$(C_1-C_2)$alkyl, halo$(C_1-C_4)$alkyl, $(C_1-C_4)$alkoxy$(C_1-C_6)$alkyl and halo$(C_1-C_4)$alkoxy$(C_1-C_6)$alkyl, or $R^1$ and $R^2$ may together represent a $(C_4-C_5)$alkylene group or a $(C_4-C_5)$alkylene group substituted with up to two substituents each independently selected from the group consisting of $(C_1-C_4)$alkyl, $(C_3-C_4)$alkenyl, $(C_3-C_4)$alkynyl, halo, halo$(C_1-C_4)$alkyl, $(C_1-C_4)$alkoxy$(C_1-C_4)$alkyl and halo$(C_1-C_4)$alkoxy$(C_1-C_4)$alkyl, so as to form a nitrogen-containing fine or six membered cyclic ring with the nitrogen to which they attach, $R^3$ is hydrogen, $(C_1-C_6)$alkyl, $(C_3-C_4)$alkenyl, $(C_3-C_4)$alkynyl, $(C_3-C_6)$cycloalkyl, $(C_3-C_6)$cycloalkyl$(C_1-C_2)$alkyl, $(C_5-C_6)$cycloalkenyl, $(C_5-C_6)$cycloalkenyl$(C_1-C_2)$alkyl, halo$(C_1-C_4)$alkyl, $(C_1-C_4)$alkoxy$(C_1-C_6)$alkyl or halo$(C_1-C_4)$alkoxy$(C_1-C_6)$alkyl, Ar is a $(C_6-C_{10})$aryl group or a $(C_6-C_{10})$ aryl group substituted with up to three substituents each independently selected from the group consisting of $(C_1-C_6)$alkyl, $(C_2-C_4)$alkenyl, $(C_3-C_4)$alkynyl, halo$(C_1-C_4)$alkyl, $(C_1-C_4)$alkoxy, halo$(C_1-C_4)$alkoxy, $(C_1-C_4)$alkoxy$(C_1-C_6)$alkyl, halo$(C_1-C_4)$alkoxy$(C_1-C_6)$alkyl, cyano, nitro, $(C_1-C_4)$alkoxycarbonyl and $(C_1-C_4)$alkylthio, and the agronomically acceptable acid addition salts and metal complexes thereof.

A preferred embodiment of this invention is the compounds, salts and complexes of Formula (I) wherein:

$R^1$ and $R^2$ are each independently selected from the group consisting of $(C_1-C_4)$alkyl, $(C_3-C_4)$alkenyl, $(C_3-C_4)$alkynyl and $(C_1-C_2)$alkoxy$(C_1-C_2)$alkyl, or $R^1$ and $R^2$ may together represent a $(C_4-C_5)$alkylene group so as to form a nitrogen-containing five or six membered cyclic ring with the nitrogen to which they attach, $R^3$ is hydrogen, $(C_1-C_4)$alkyl, $(C_5-C_6)$cycloalkyl, halo$(C_1-C_2)$alkyl, $(C_1-C_2)$alkoxy$(C_1-C_2)$alkyl or halo$(C_1-C_2)$alkoxy$(C_1-C_2)$alkyl, and Ar is naphthyl or, preferably, phenyl, or naphthyl or, preferably, phenyl substituted with up to two substituents each independently selected from the group consisting of $(C_1-C_4)$alkyl, $(C_2-C_4)$alkenyl, $(C_3-C_4)$alkynyl, halo$(C_1-C_2)$alkyl, $(C_1-C_4)$alkoxy, halo($C_1$–$C_2$)alkoxy, ($C_1$–$C_2$)alkoxy($C_1$–$C_4$)alkyl and halo($C_1$–$C_2$)alkyl.

A more preferred embodiment of this invention is the compounds, salts and complexes of Formula (I) wherein:

$R^1$ and $R^2$ are each independently selected from ($C_1$–$C_4$)alkyl or may together represent a ($C_4$–$C_5$)alkylene group so as to form a nitrogen-containing five or six membered cyclic ring with the nitrogen to which they attach, $R^3$ is hydrogen, ($C_1$–$C_4$)alkyl, ($C_5$–$C_6$)cycloalkyl or ($C_1$–$C_2$)alkoxy($C_1$–$C_2$)alkyl, and Ar is phenyl or phenyl substituted with up to two substituents each independently selected from the group consisting of ($C_1$–$C_2$)alkyl, halo($C_1$–$C_2$)alkyl, ($C_1$–$C_2$)alkoxy, halo($C_1$–$C_2$)alkoxy and ($C_1$–$C_2$)alkoxy($C_1$–$C_2$)alkyl.

An even more preferred embodiment of this invention is the compounds, salts and complexes of Formula (I) wherein:

$R^1$ and $R^2$ are each independently selected from a ($C_1$–$C_4$)alkyl group, $R^3$ is hydrogen, ($C_1$–$C_4$)alkyl or ($C_1$–$C_2$)alkoxy($C_1$–$C_2$)alkyl, and Ar is phenyl or phenyl substituted with up to two substituents each independently selected from methyl, ethyl, methoxy and ethoxy.

A most preferred embodiment of this invention is the compounds, salts and complexes of Formula (I) wherein $R^1$ and $R^2$ are each independently methyl or ethyl, $R^3$ is hydrogen, methyl, isopropyl or methoxymethyl, and Ar is phenyl, 2,6-dimethylphenyl or 2-methoxy-5-methylphenyl.

The term "Ar" (aryl) as used in the present specification means an aromatic ring structure of six to ten carbon atoms, preferably a phenyl or naphthyl group. Typical aryl groups encompassed by this invention are phenyl, naphthyl, 2-methylphenyl, 3-methylphenyl, 4-methylphenyl, 2,6-dimethylphenyl, 2,4-dimethylphenyl, 2,3-dimethylphenyl, 2-ethyl-6-methylphenyl, 2isobutyl-6-methylphenyl, 4-t-butylphenyl, 2-ethylnaphthyl, 4-isopropylphenyl, 4-sec-butylphenyl, 2,4,6-trimethylphenyl, 2-methoxy-5-methylphenyl, 3-methoxy-2-methylphenyl, 2-methoxy-3-methylphenyl, 2-ethoxy-5-methylphenyl, 2-isobutoxy-5-methylphenyl, 2-methoxy-5-ethylphenyl, 2-methoxy-5-n-propylphenyl, 5-n-hexyl-2-methoxyphenyl, 4-allylphenyl, 2-vinylphenyl, 2-methyl-4-vinylphenyl, 2-propargylphenyl, 2-methyl-4-propargylphenyl, 2-methoxy-5-(trifluoromethyl)phenyl, 2-(difluoromethoxy)-5-methylphenyl, 2-(difluoromethoxy)-3-methylphenyl, 4-(trifluoromethyl)phenyl, 2-(2-chloroethyl)phenyl, 4-nitrophenyl, 2-cyanophenyl, 2-cyano-4-methylphenyl, 2-nitro-4-(trifluoromethyl)phenyl, 4-(ethoxycarbonyl)phenyl, 4-isopropyl-2-(methylthio)phenyl, 4-t-butoxyphenyl, 4-n-propylphenyl, 2-nitrophenyl, 2,4-dicyanophenyl, 4-(n-butylthio)phenyl and 5-methyl-2-(trifluoromethoxy)phenyl.

Alkyl includes straight and branched chain alkyl groups, for example ($C_1$–$C_6$)alkyl such as methyl, ethyl, n-propyl, isopropyl, n-butyl, isobutyl, sec-butyl, t-butyl, n-pentyl, isopentyl, neopentyl, 2,2-dimethylpropyl, n-hexyl, isohexyl or 2,2-dimethylbutyl.

Alkenyl is, for example, ($C_2$–$C_4$)alkenyl such as vinyl, allyl, methallyl and 2-butenyl.

Alkynyl is, for example, ($C_3$–$C_4$)alkynyl such as propargyl and 2-butynyl.

Cycloalkyl is, for example, ($C_3$–$C_6$)cycloalkyl such as cyclopropyl, cyclopentyl and cyclohexyl.

Cycloalkylalkyl is, for example, ($C_3$–$C_6$)cycloalkyl($C_1$–$C_2$)alkyl such as cyclopropylmethyl, 2-(cyclopentyl)ethyl and cyclohexylmethyl.

Cycloalkenyl is, for example, ($C_5$–$C_6$)cycloalkenyl such as cyclopenten-3-yl and cyclohexen-3-yl.

Cycloalkenylalkyl is, for example, ($C_5$–$C_6$)cycloalkenyl($C_1$–$C_2$)alkyl such as cyclopenten-3-ylmethyl and 2-(cyclohexen-3-yl)ethyl.

Halo means fluoro, chloro, bromo and iodo.

Haloalkyl is, for example, halo($C_1$–$C_4$)alkyl such as chloromethyl, fluoromethyl, difluoromethyl, trifluoromethyl, 1-chloroethyl, 1,1-difluoroethyl, 3-chloropropyl, 1-bromo-2-methylpropyl, 2,3-dichloropropyl, 3-iodopropyl and 4-bromobutyl.

Alkoxyalkyl is, for example, ($C_1$–$C_4$)alkoxy($C_1$–$C_6$)alkyl such as methoxymethyl, ethoxymethyl, isopropoxymethyl, t-butoxymethyl, 2-methoxyethyl, 3-methoxypropyl, 4-methoxybutyl, 4-methoxy-2-methylbutyl, 6-methoxyhexyl, 2-ethoxyethyl, 3-ethoxypropyl, 5-ethoxypentyl and 4-(isobutoxy)butyl.

Haloalkoxyalkyl is, for example, halo($C_1$–$C_4$)alkoxy($C_1$–$C_6$)alkyl such as trifluoromethoxymethyl, difluoromethoxymethyl, chloromethoxymethyl, bromomethoxymethyl, 2-(2-chloroethoxy)ethyl, 2-(1,1-difluoroethoxy)ethyl, 3-(trifluoromethoxy)propyl, 4-(2-bromopropoxy)-2-methylpentyl and 6-(4-chlorobutoxy)hexyl.

Alkylene is, for example, a ($C_4$–$C_5$)alkylene such as butylene (—$CH_2CH_2CH_2CH_2$—) and pentylene (—$CH_2CH_2CH_2CH_2CH_2$—).

Alkoxycarbonyl is for example, a ($C_1$–$C_4$)alkoxycarbonyl such as ethoxycarbonyl.

Alkylthio is, for example, a ($C_1$–$C_4$)alkylthio such as methylthio and isopropylthio.

This invention also includes the acid addition salts of the compounds of formula (I) wherein the anionic counterion of the acid is selected in such a manner that the sum of the valence charges of the protonated triazole compound and the anion equals zero.

This invention further includes the metal salt complexes of the compounds of formula (I) wherein the metal is a cation selected from Groups IIA, IVA, IB, IIB, VIB, VIIB and VIII of the Periodic Table and the anionic counterion of the metal is selected in such a manner that the sum of the valence charges of the cation and anion equals zero.

The 1-(disubstituted carbamoyl)-3-(N-arylsulfonamido)-1,2,4-triazoles of this invention can be prepared by conventional synthetic methods. For example, a 3-(N-arylsulfonamido)-1,2,4-triazole of the general formula (II) can be reacted with a carbamoyl halide of the general formula (III):

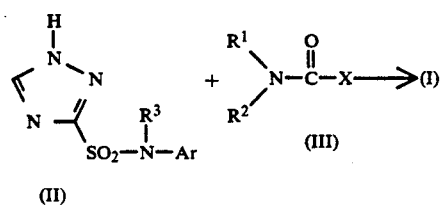

in which $R^1$, $R^2$, $R^3$ and Ar are as described for Formula (I) and X is chlorine, bromine or fluorine, preferably chlorine. The reaction is suitably effected in an aqueous medium or in the presence of an organic solvent which is inert to the reactants. Such solvents include aromatic hydrocarbons such as toluene or xylene, halogenated hydrocarbons such as methylene chloride or chlorobenzene, ethers such as diethyl ether or tetrahydrofuran, ketones such as acetone or methyl ethyl ketone, organic bases such as pyridine, triethyl amine or N,N-dimethylaniline, acetonitrile, N,N-dimethylformamide and dimethyl sulfoxide. The reaction can be run at a temperature from about the freezing point to the boiling point of the solvent, preferably from about 0° C. to about 150° C., for a time from about 10 minutes to about 48 hours. The reaction is conducted in the presence of an acid acceptor for the hydrogen halide by-product which is generated during the reaction. Examples of such acid acceptors include inorganic bases such as sodium hydroxide, potassium hydroxide, sodium carbonate and sodium bicarbonate or organic bases such as triethyl amine or pyridine. Preferred are the organic bases, such as triethyl amine or pyridine, since they can function as a convenient solvent for the reaction. The usual equivalent ratio of reactants is from about a 1 to 1 ratio of a triazole compound of formula (II) to a carbamoyl halide of formula (III) to about a 1 to 1.5 ratio of a triazole compound of formula (II) to a carbamoyl halide of formula (III). An equivalent ratio of from about a 1 to 1 ratio of a triazole compound of formula (II) to the acid acceptor to about a 1 to 10 ratio of a triazole compound of formula (II) to the acid acceptor may be conveniently employed. In a slight variation of this procedure, the triazole compound of formula (II) can be reacted with an inorganic base, preferably a Group IA metal hydroxide such as sodium or potassium, and converted to a triazole salt in accordance with known methods prior to the reaction with a carbamoyl halide of formula (III), thus making the use of an acid acceptor unnecessary.

The carbamoyl halides of formula (III) may be prepared by reacting a secondary amine of the formula $R^1NHR^2$, in which $R^1$ and $R^2$ are as described for formula (I), with a carbonyl halide $COX_2$ where X is chlorine, bromine or fluorine, preferably chlorine, in accordance with known methods.

The compounds of formula (I) also can be prepared by reacting a carbamoyl halide of formula (IV) in which $R^3$ and Ar are as described for formula (I) and X is as described for formula (III) with a secondary amine of the formula $R^1NHR^2$ in which $R^1$ and $R^2$ are as described for formula (I). The reaction is suitably effected in the presence of an

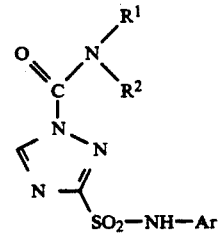

organic solvent, which is inert to the reactants, such as those described for the reaction of compounds of formula (II) with compounds of formula (III). Preferred are the organic bases, such as triethyl amine or pyridine, since they can function as a convenient hydrogen halide acceptor for the reaction.

The carbomoyl halides of formula (IV) can be prepared from triazoles of formula (II) by reaction with a carbonyl halide $COX_2$, preferably phosgene, in accordance with known methods.

The 3-sulfonamido triazoles of formula (II) can be prepared by reacting a 1,2,4-triazole-3-sulfonyl halide, preferably the chloride, with an amine of the general formula $R^3NHAr$ wherein $R^3$ and Ar are as described in formula (I). Reaction conditions which are generally employed are the same as those described previously for the reaction of compounds of formula (II) with compounds of formula (III) to produce compounds of formula (I).

An alternative method for providing compounds of formula (I) is available when $R^3$ is hydrogen as shown in formula (IA). The

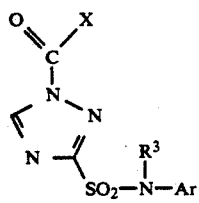

compound of formula (IA) can be alkylated using an appropriate alkylating agent of the formula $R^3Y$ wherein $R^3$ is described as previously for formula (I), with the exception that $R^3$ is not hydrogen, and Y is a chloride, bromide, iodide, methylsulfonate, phenylsulfonate, 4-tolysulfonate or any other leaving group capable of effecting the desired N-alkylation reaction, for example, methyl iodide or chloromethyl methyl ether. A standard N-alkylation reaction process, for example, using sodium hydride in an aprotic polar solvent such as N,N-dimethylformamide or diethyl ether or in an aromatic hydrocarbon solvent such as toluene or xylene, can be employed to obtain the desired compound of formula (I) wherein $R^3$ is not hydrogen. The reaction is carried out at a temperature of from about $-10°$ C. to about 250° C., preferably at a temperature of from about 20° C. to about 100° C.

The acid addition salts of the 1,2,4-triazoles of this invention can be prepared by techniques which are well known in the art. A 1,2,4-triazole of formula (I) can be dissolved in an appropriate polar solvent, for example, diethyl ether, tetrahydrofuran, ethanol, methanol or combinations thereof, and reacted at a temperature from about 0° C. to about 50° C. with an equivalent or excess amount of a mineral or organic acid, for example, hydrochloric, sulfuric, nitric, phosphoric and acetic which may or may not be dissolved in a solvent common to the solvent of the triazole solution. The mixture is then either cooled or evaporated to give an acid addition salt of the compounds of formula (I) which can be either used as such or recrystallized from an appropriate solvent or combination of appropriate solvents, for example, methanol, chloroform, acetone, diethyl ether and tetrahydrofuran.

The metal salt complexes of the 1,2,4-triazoles of this invention can be prepared by adding dropwise, with stirring, a stoichiometric amount of a metal salt, for example, zinc (II) chloride and copper (II) chloride, dissolved in an appropriate solvent or combination of solvents to a solution of the 1,2,4-triazole. The reaction mixture is briefly stirred and the solvent is removed, for example, by distillation, to give a metal salt complex of the compounds of formula (I).

An alternative preparation of these metal salt complexes involves mixing stoichiometric or excess amounts of the metal salt and a triazole of formula (I) in a solvent containing adjuvants just prior to spraying the plants. Adjuvants that may be included in this in-situ formulation preparation are detergents, emulsifiers, wetting agents, spreading agents, dispersing agents, stickers and adhesives which are used in agricultural applications.

Solvents that can be utilized in both of these procedures to prepare metal salt complexes include any polar solvent, for example, water, methanol, ethanol, isopropanol or ethylene glycol and any aprotic dipolar solvent, for example, dimethyl sulfoxide, acetonitrile, dimethylformamide, nitromethane or acetone.

The metal salt cations that can be used in these procedures can be selected from the group consisting of calcium, magnesium, manganese, copper, nickel, zinc, iron, cobalt, tin, cadmium, mercury, chromium, lead and barium.

Examples of anions that can be used as the counterion in the metal salt include, but are not limited to, chloride, bromide, iodide, sulfate, bisulfate, phosphate, nitrate, perchlorate, carbonate, bicarbonate, hydrosulfide, hydroxide, acetate, oxalate, malate and citrate.

The following examples are provided to illustrate the present invention.

TABLE 1

Structure and Melting Point (M.P.) of Typical Compounds

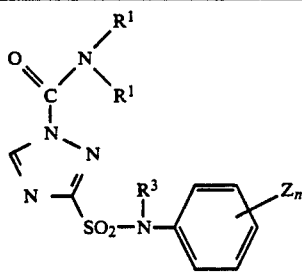

| Ex. No. | $R^1$ | $R^3$ | $Z_n$ | M.P. °C. |
|---|---|---|---|---|
| 1 | $C_2H_5$ | H | H | 121–127.5 |
| 2 | $C_2H_5$ | $CH_3$ | H | 61–66 |
| 3 | $C_2H_5$ | H | 2-$CH_3$, 6-$CH_3$ | 93–96 |
| 4 | $C_2H_5$ | $CH_3$ | 2-$CH_3$, 6-$CH_3$ | 97–103 |
| 5 | $C_2H_5$ | $CH_2OCH_3$ | 2-$CH_3$, 6-$CH_3$ | 117–119 |
| 6 | $CH_3$ | H | 2-$OCH_3$, 5-$CH_3$ | 121–122 |
| 7 | $CH_3$ | $CH(CH_3)_2$ | H | 130–132 |
| 8 | $C_2H_5$ | H | 2-$OCH_3$, 5-$CH_3$ | 110–112 |
| 9 | $C_2H_5$ | $CH(CH_3)_2$ | H | 117–118 |
| 10 | $C_2H_5$ | $CH_3$ | 2-$OCH_3$, 5-$CH_3$ | 94–97 |
| 11 | $C_2H_5$ | $CH_2OCH_3$ | 2-$OCH_3$, 5-$CH_3$ | 125–127 |

EXAMPLE 1

Preparation of
1-(N,N-Diethylcarbamoyl)-3-(N-Phenylsulfonamido)-1,2,4-Triazole a. Preparation of 1,2,4-Triazole-3-Sulfonyl Chloride To a flask was added 500 milliliters (ml) of 2 molar hydrochloric acid at 0° C. followed by 30.3 grams (g) of 1,2,4-triazole-3-thiol. The resulting solution was vigorously stirred and chlorine gas was passed into it over one hour while maintaining the temperature of the exothermic reaction at 0° C. The solid which formed was filtered off, washed with water at 0° C. and partially dried to yield 26 g of the desired intermediate.

b. Preparation of 3-(N-Phenylsulfonamido)-1,2,4-Triazole

To a flask was added 69 g of aniline and 150 ml of water at 20° C. The mixture was stirred vigorously and the 26 g of 1,2,4-triazole-3-sulfonyl chloride was added over 10 minutes while maintaining the temperature of the exothermic reaction below 23° C. The resulting thick paste in a colorless solution was stirred at 20° C. for 40 minutes and then approximately 40 ml of concentrated hydrochloric acid was added which lowered the pH from about 5 to 4. During the acid addition, the temperature of the solution rose to 38° C. with the thick paste becoming granular and finally frothy. The mixture was allowed to cool to 24° C., suction filtered and the solid washed with water and dried yielding 27 g of the desired intermediate.

c. Preparation of 1-(N,N-Diethylcarbamoyl)-3-(N-Phenylsulfonamido)-1,2,4-Triazole To a flask was added 60 ml of dry pyridine followed by 20.0 g of 3-(N-phenylsulfonamido)-1,2,4-triazole. The resulting solution was stirred at room temperature and 12.5 ml of diethylcarbamoyl chloride was added in one portion. The mixture was stirred under dry nitrogen at room temperature for 16 hours with the resultant formation of a precipitate. The mixture was warmed slightly using a bath at equal to or less than 40° C. to redissolve the precipitate and the resulting orange solution was poured into 300 ml of cold 2 molar hydrochloric acid and 300 ml of ethyl acetate. The organic layer was separated, washed sequentially with 150 ml of 2 molar hydrochloric acid, 150 ml of water and 150 ml of saturated aqueous sodium chloride solution (brine), dried with sodium sulfate, filtered and concentrated until crystals began to form in the solution. The volume of solid plus solution was made up to 100 ml with ethyl acetate and then 200 ml of hexane was added. The mixture was cooled and the solid was filtered off and dried yielding 25.9 g of the desired product as a pale pink solid.

EXAMPLE 2

Preparation of
1-(N,N-Diethylcarbamoyl)-3-(N-Methyl-N-Phenylsulfonamido)-1,2,4-Triazole To a flask was added 0.68 g of 60% sodium hydride in oil. After washing three times with 5 ml portions of hexane in a dry nitrogen atmosphere to remove the oil, 10 ml of dry N,N-dimethylformamide was added followed by a dropwise addition of a mixture of 1-(N,N-diethylcarbamoyl)-3-(N-phenylsulfonamido)-1,2,4-triazole in 10 ml of dry N,N-dimethylformamide over five minutes while keeping the temperature of the exothermic reaction at 15° to 25° C. The mixture was stirred at 20° C. for a further 20 minutes and a clear solution resulted which was then cooled to 0° C. Iodomethane, 2.5 g, was added over 30 seconds causing a white precipitate to form which made the mixture very viscous. The mixture was stirred for 30 minutes as it warmed to 22° C. and another 1.1 g of iodomethane was added in one portion. The mixture was stirred another two hours at room temperature under a dry nitrogen atmosphere and then dissolved in 100 ml of water and 100 ml of ethyl acetate. The organic layer was separated, washed three times with 100 ml of water and then with 50 ml of saturated brine solution, dried over sodium sulfate, filtered and concentrated to give a colorless, viscous liquid. Upon standing overnight, a white solid formed yielding 4.81 g of the desired product.

EXAMPLE 3

Preparation of
1-(N,N-Diethylcarbamoyl)-3-[N-(2,6-Dimethylphenyl)-sulfonamido]-1,2,4-Triazole This example was prepared according to the procedure of Example 1 except that 2,6-dimethylaniline was substituted for aniline.

EXAMPLE 4

Preparation of
1-(N,N-Diethylcarbamoyl)-3-[N-(2,6-Dimethylphenyl)-N-Methylsulfonamido]-1,2,4-Triazole This example was prepared according to the procedure of Example 2 except that 1-(N,N-diethylcarbamoyl)-3-[N-(2,6-dimethylphenyl)sulfonamido]-1,2,4-triazole was substituted for 1-(N,N-diethylcarbamoyl)-3-(N-phenylsulfonamido)-1,2,4-triazole.

EXAMPLE 5

Preparation of
1-(N,N-Diethylcarbamoyl)-3-[N-(2,6-Dimethylphenyl)-N-Methoxymethylsulfonamido]-1,2,4-Triazole This example was prepared according to the procedure of Example 4 except that chloromethyl methyl ether was substituted for iodomethane.

EXAMPLE 6

Preparation of
1-(N,N-Dimethylcarbamoyl)-3-[N-(2-Methoxy-5-Methylphenyl)sulfonamido]-1,2,4-Triazole a. Preparation of 3-[N-(2-Methoxy-5-Methylphenyl)-sulfonamido]-1,2,4-Triazole To a flask was added 150 ml of water, which was warmed to 40° C., followed by 20.6 g of 2-methoxy-5-methylaniline. The mixture was stirred vigorously and 25 g of 1,2,4-triazole-3-sulfonyl chloride was added followed by the addition of 31.4 ml of triethylamine. The resulting reaction mixture was stirred for 24 hours at room temperature and then suction filtered to obtain 24.23 g of brown solid which was placed under high vacuum for 6 hours to obtain 19.79 g of material. The solid was triturated in 100 ml of methylene chloride in order to remove the excess 2-methoxy-5-methylaniline which was present and then filtered to obtain 10.27 g of the desired intermediate.

b. Preparation of 1-(N,N-Dimethylcarbamoyl)-3-[N-(2-Methoxy-5-Methylphenyl)sulfonamido]-1,2,4-Triazole Following the procedure of Example 1c except that dimethylcarbamoyl chloride was substituted for diethylcarbamoyl chloride, the intermediate from Example 6a was used to prepare 10.21 g of the desired product.

EXAMPLE 7

Preparation of
1-(N,N-Dimethylcarbamoyl)-3-(N-Isopropyl-N-Phenylsulfonamido)-1,2,4-Triazole This example was prepared according to the procedure of Example 6 except that N-isopropylaniline was substituted for 2-methoxy-5-methylaniline.

EXAMPLE 8

Preparation of
1-(N,N-Diethylcarbamoyl)-3-[N-(2-Methoxy-5-Methylphenyl)sulfonamido]-1,2,4-Triazole This example was prepared using the procedures of Examples 6a and 1c except that the intermediate from Example 6a was used in place of the intermediate from Example 1b in Example 1c.

EXAMPLE 9

Preparation of
1-(N,N-Diethylcarbamoyl)-3-(N-Isopropyl-N-Phenyl-sulfonamido)-1,2,4-Triazole This example was prepared using the procedures of Example 6a, except for the substitution of N-isopropylaniline for 2-methoxy-5-methylaniline, and Example 1c.

EXAMPLE 10

Preparation of
1-(N,N-Diethylcarbamoyl)-3-[N-(2-Methoxy-5-Methylphenyl)-N-Methylsulfonamido]-1,2,4-Triazole This example was prepared using the procedure of Example 2 except that 1-(N,N-diethylcarbamoyl)-3-[N-(2-methoxy-5-methylphenyl)sulfonamido-1,2,4-triazole was substituted for 1-(N,N-diethylcarbamoyl)-3-(N-phenylsulfonamido)-1,2,4-triazole.

EXAMPLE 11

Preparation of
1-(N,N-Diethylcarbamoyl)-3-[N-Methoxymethyl-N-(2-Methoxy-5-Methylphenyl)sulfonamido]-1,2,4-Triazole This example was prepared using the procedure of Example 10 except that chloromethyl methyl ether was substitued for iodomethane.

The following test procedure was employed to assess the herbicidal activity of the compounds of the invention.

Seeds of selected plants were planted in flats or pots. For pre-emergence tests, immediately after planting, the test compound was sprayed directly onto the soil surface. The flats or pots were then placed in a greenhouse and watered. For postemergence tests, the seeds were allowed to germinate and grow in a greenhouse for 10 to 21 days. Before application, each series of test plants were selected for uniformity, size and stage of development. The test plants were then treated with the test compound. The plants for postemergence tests were returned to the greenhouse and then watered. Test species employed were:

| CODE | COMMON NAME | SCIENTIFIC NAME |
|------|-------------|-----------------|
| | MONOCOTS | |
| BYG | Barnyard grass | Echinochloa crus-galli |
| FOX | Green Foxtail | Setaria viridis |
| JON | Johnsongrass | Sorghum halepense |
| NUT | Nutsedge | Cyperus esculentus |
| WO | Wild Oat | Avena fatua |
| | DICOTS | |
| CKL | Cocklebur | Xanthium strumarium |
| MG | Morningglory | Ipomoea lacunosa |
| PIG | Pigweed | Amaranthus retroflexus |
| SMT | Smartweed | Polygonum lapathifolium |
| VEL | Velvetleaf | Abutilon theophrasti |

The compound to be evaluated was dissolved in an appropriate solvent, usually acetone, and sprayed over the flats or pots using a carrier volume equivalent to 25 or 50 gallons per acre at the rate of application in pounds per acre (lb/A) specified in the table. About two or three weeks after application of the test compound, the state of growth of the plants was observed. Each species was evaluated on a scale of 0-100 in which 0 equals no activity and 100 equals total control.

The results are shown in Table 2.

TABLE 2

Herbicidal Test Data for Examples 1-11

| Ex. No. | Appl. Rate, Type | Lb/A | CKL | MG | PIG | SMT | VEL | BYG | FOX | JON | NUT | WO |
|---|---|---|---|---|---|---|---|---|---|---|---|---|
| 1. | Pre | 4.00 | 0 | 0 | —* | 0 | 0 | 66 | 36 | 0 | 0 | 0 |
|  | Post | 4.00 | 0 | 0 | 0 | 0 | 0 | 0 | 0 | 0 | 0 | 0 |
| 2. | Pre | 2.00 | 0 | 15 | 0 | 86 | 95 | 100 | 100 | 95 | 90 | 80 |
|  | Post | 2.00 | 0 | 0 | 6 | 0 | 0 | 71 | 0 | 0 | 0 | 0 |
| 3. | Pre | 4.00 | 100 | 0 | 100 | 100 | 100 | 100 | 100 | 0 | 0 | 0 |
|  | Post | 4.00 | 100 | 0 | 100 | 100 | 100 | 100 | 100 | 0 | 0 | 0 |
| 4. | Pre | 2.00 | —* | 0 | 0 | 0 | 0 | 100 | 100 | 100 | 31 | 25 |
|  | Post | 2.00 | 0 | 10 | 0 | 0 | 0 | 66 | 0 | 0 | 0 | 0 |
| 5. | Pre | 2.00 | —* | 0 | 20 | 0 | 0 | 100 | 98 | 100 | 0 | 0 |
|  | Post | 2.00 | 0 | 0 | 0 | 0 | 0 | 21 | 0 | 0 | 0 | 0 |
| 6. | Pre | 4.00 | 0 | 0 | —* | 0 | 0 | 98 | 100 | 61 | 0 | 41 |
|  | Post | 4.00 | 0 | 0 | 10 | 0 | 0 | 45 | 15 | 45 | 0 | 21 |
| 7. | Pre | 4.00 | —* | 0 | —* | 0 | 0 | 100 | 100 | 90 | 0 | 51 |
|  | Post | 4.00 | 0 | 20 | 0 | 0 | 0 | 31 | 31 | 0 | 0 | 0 |
| 8. | Pre | 2.00 | 65 | 16 | —* | 0 | 0 | 100 | 100 | 98 | 0 | 0 |
|  | Post | 2.00 | 65 | 0 | 0 | 0 | 0 | 0 | 0 | 0 | 0 | 0 |
| 9. | Pre | 2.00 | 0 | 0 | 0 | 0 | 0 | 100 | 100 | 90 | 0 | 25 |
|  | Post | 2.00 | 0 | 0 | 0 | 0 | 0 | 0 | 0 | 0 | 0 | 0 |
| 10. | Pre | 2.00 | 0 | —* | 0 | 0 | 0 | 100 | 98 | 98 | 0 | 35 |
|  | Post | 2.00 | 0 | 0 | 0 | 0 | 0 | 0 | 0 | 0 | 0 | 0 |
| 11. | Pre | 2.00 | 0 | 0 | —* | 0 | 0 | 100 | 0 | 25 | 0 | 0 |
|  | Post | 2.00 | 0 | 0 | 0 | 0 | 0 | 0 | 0 | 0 | 0 | 0 |

*Not Tested

The compounds of this invention are active herbicidally on monocot and dicot weeds in either pre- or postemergence applications. In general, they require lower doses to control monocot weeds preemergence. In particular, several annual grasses, such as *Echinochloa crusgalli, Setaria viridis* and *Sorghum halepense* are especially sensitive. The compounds of this invention generally show selectivity to several agronomically important crops such as corn, soybeans, wheat, rice, cotton and sugarbeets. The compounds of this invention also possess utility for non-selective uses.

The invention is most effective when the compounds are formulated in an appropriate carrier, such that the dissolved or dispersed compound is readily applied over the plants or soil in a uniform manner.

The invention is also effective when used as a part of a mixture of herbicides formulated in the above manner.

The present herbicides may be applied in any amount which will give the required control of the undesired plants. Generally a rate of application of the herbicides of the invention is from about 0.001 to about 8 pounds per acre and preferably from about 0.01 to about 4 pounds of the compound per acre. Most preferably a rate from about 0.1 to about 2 pounds per acre is used.

The compounds of the present invention are useful both as preemergence and postmergence herbicides. Preemergence herbicides may be applied to the soil surface or incorporated into the soil. Postemergence herbicides are those which are applied after the plants have emerged and during their growth period. The compounds of the present invention may be applied to the soil surface prior to plant emergence or incorporated into the soil or other growth medium prior to planting. This incorporation can be carried out by any convenient means, including by simply mixing with the soil, by applying the compound to the surface of the soil and then disking or dragging into the soil to the desired depth, or by employing a liquid carrier to accomplish the necessary penetration and impregnation.

A compound of the present invention can be applied postemergence to the growth medium or to plants to be treated either by itself, or, as is generally done, as a component in a herbicidal composition or formulation which also comprises an agronomically acceptable carrier.

By agronomically acceptable carrier is meant any substance which can be used to dissolve, disperse or diffuse a herbicidal compound in the composition without impairing the effectiveness of the herbicidal compound and which by itself has no detrimental effect on the soil, equipment, crops or agronomic environment. Mixtures of the compounds of the present invention may also be used in any of these herbicidal formulations. The herbicidal compositions of the invention can be either solid or liquid formulations or solutions. For example, the compounds can be formulated as wettable powders, solutions, emulsifiable concentrates, dusts, granular formulations, aerosols, water dispersable granular formulations or flowable concentrates as is known to one in the art. In such formulations, the compounds are extended with a liquid or solid carrier and, when desired, suitable surfactants or emulsifiers are incorporated.

It is usually desirable, particularly in postemergence applications, to include adjuvants such as wetting agents, spreading agents, dispersing agents, sticking agents, adhesives and the like, in accordance with agricultural practices. Examples of adjuvants which are commonly used in the art can be found in the John W. McCutcheon, Inc. publication "Detergents and Emulsifiers Annual."

The compounds of this invention can be dissolved in any appropriate solvent. Examples of solvents which are useful in the practice of this invention include water, alcohols, ketones, aromatic hydrocarbons, halogenated hydrocarbons, dimethylformamide, dioxane, dimethyl sulfoxide and the like. Mixtures of these solvents can also be used. The concentration of compound in the solution can vary from about 2% to about 98%.

The compounds of the present invention can also be mixed with fertilizers or fertilizing materials before their application. In one type of solid fertilizing composition in which the compounds may be used, particles of a fertilizer or fertilizing ingredients, such as ammonium sulfate, ammonium nitrate or ammonium phosphate can be coated with one or more of the herbicides. The solid herbicide and solid fertilizing material may also be admixed in blending or mixing equipment, or they can be incorporated with fertilizers in granular formulations. Any relative proportion of herbicide and fertilizer can be used which is suitable for the crops and weeds to be treated.

The compounds of the present invention may be applied as herbicidal sprays by methods commonly employed, such as conventional high-gallonage hydraulic sprays, low gallonage sprays, air blast spray, aerial sprays and dusts. For some applications, two or more of the compounds of the instant invention may be combined, thereby providing additional advantages and effectiveness. When mixtures of the compounds of the invention are used, the relative proportion of each compound used will depend on the relative efficacy of the compounds in the mixture with respect to the plants to be treated.

For some applications, one or more other herbicides may be added of the herbicides of the present invention, thereby providing additional advantages and effectiveness. When mixtures of herbicides are employed, the relative proportions which are used will depend upon the relative efficacy of compounds in the mixture with respect to the plants to be treated. Examples of other herbicides which can be combined with those of the present invention include:

Carboxylic Acids and Derivatives 2,3,6-trichlorobenzoic acid and its salts; 2,3,5,6-tetrachlorobenzoic acid and its salts; 2-methoxy-3,5,6-trichlorobenzoic acid and its salts; 2-methoxy-3,6-dichlorobenzoic acid and its salts; 2-methyl-3,6-dichlorobenzoic acid and its salts; 2,3-dichloro-6-methylbenzoic acid and its salts; 2,4-dichlorophenoxyacetic acid and its salts and esters; 2,4,5-trichlorophenoxyacetic acid and its salts and esters; 2-methyl-4-chlorophenoxyacetic acid and its salts and esters; 2-(2,4,5-trichlorophenoxy)propionic acid and its salts and esters; 4-(2,4-dichlorophenoxy)butyric acid and its salts and esters; 4-(2-methyl-4-chlorophenoxy)butyric acid and its salts and esters; 2,3,6-trichlorophenylacetic acid and its salts; 3,6-endoxohexahydrophthalic acid and its salts; dimethyl 2,3,5,6-tetrachloroterephthalate; trichloroacetic acid and its salts; 2,2-dichloropropionic acid and its salts; 2,3-dichloroisobutyric acid and its salts; isopropylammonium 2-(4-isopropyl-5-methyl-5-oxo-2-imidazolin-2-yl)nicotinate; 2-[4,5-dihydro-4-methyl-4-(1-methylethyl)-5-oxo-1H-imidazol-2-yl]-3-quinolinecarboxylic acid; m-toluic acid, 6-(4-isopropyl-4-methyl-5-oxo-2-imidazolin-2-yl)-, methyl ester and p-toluic acid, 6-(4-isopropyl-4-methyl-5-oxo-2-imidazolin-2-yl)-, methyl ester; N-(phosphomethyl)glycine isopropylammonium salt; [3,5,6-trichloro-(2-pyridinyl)oxy]acetic acid; 3,7-dichloro-8-quinolinecarboxylic acid; ammonium DL-homoalanin-4-yl(methyl)phosphinate.

Carbamic Acid Derivatives ethyl N,N-di(n-propyl)thiolcarbamate; n-propyl N,N-di(n-propyl)thiolcarbamate; ethyl N-ethyl-N-(n-butyl)thiolcarbamate; n-propyl N-ethyl-N-(n-butyl)thiolcarbamate; 2-chloroallyl N,N-diethyldithiocarbamate; isopropyl N-phenylcarbamate; isopropyl N-(m-chlorophenyl)carbamate; 4-chloro-2-butynyl-N-(m-chlorophenyl)carbamate; methyl N-(3,4-dichlorophenyl)carbamate; dinitro-o-(sec-butyl)phenol and its salts; pentachlorophenol and its salts; S-(4-chlorobenzyl)-N,N-diethylthiolcarbamate.

Substituted Ureas 2-chloro-N-[(4-methoxy-6-methyl-1,3,5-triazin-2-yl)aminocarbonyl]-benzenesulfonamide; 3-(3,4-dichlorophenyl)-1,1-dimethylurea; 3-phenyl-1,1-dimethylurea; 3-(3,4-dichlorophenyl)-3-methoxy-1,1-dimethylurea; 3-(4-chlorophenyl)-3-methoxy-1,1-dimethylurea; 3-(3,4-dichlorophenyl)-1-n-butyl-1-methylurea; 3-(3,4-dichlorophenyl)-1-methoxy-1-methylurea; 3-(4-chlorophenyl)-1-methoxy-1-methylurea; 3-(3,4-dichlorophenyl)-1,1,3-trimethylurea; 3-(3,4-dichlorophenyl)diethylurea; dichloral urea; methyl 2-[[[[(4,6-dimethyl-2-pyrimidinyl)amino]carbonyl]amino]sulfonyl]-benzoate; N-((6-methoxy-4-methyl-1,3,5-triazin-2-yl)aminocarbonyl)-2-(2-chloroethoxy)benzenesulfonamide; 2-[[[(4-chloro-6-methoxypyrimidine-2-yl)aminocarbonyl]amino]sulfonyl]benzoic acid, ethyl ester; methyl 2-[[[[(4-methoxy-6-methyl-1,3,5-triazin-2-yl)amino]carbonyl]amino]sulfonyl]benzoate; methyl 3-[[(4-methoxy-6-methyl-1,3,5-triazin-2-yl)aminocarbonyl]aminosulfonyl]-2-thiophenecarboxylate; methyl 2-[[[[(4,6-dimethoxypyrimidin-2-yl)amino]carbonyl]amino]sulfonyl]methyl]benzoate; methyl 2-[[[[(4-methoxy-6-methyl-1,3,5-triazin-2-yl)methylamino]carbonyl]amino]sulfonyl]benzoate.

Substituted Triazines 2-chloro-4,6-bis(ethylamino)-s-triazine; 2-chloro-4-ethylamino-6-isopropylamino-s-triazine; 2-chloro-4,6-bis(methoxy-n-propylamino)-s-triazine; 2-methoxy-4,6-bis(isopropylamino)-s-triazine; 2-chloro-4-ethylamino-6-(3-methoxy-n-propylamino)-s-triazine; 2-methylmercapto-4,6-bis(isopropylamino)-s-triazine; 2-methylmercapto-4,6-bis(ethylamino)-2-triazine; 2-methylmercapto-4-ethylamino-6-isopropylamino-s-triazine; 2-chloro-4,6-bis(isopropylamino)-s-triazine; 2-methoxy-4-ethylamino-6-isopropylamino-s-triazine; 2-methylmercapto-4-(2-methoxyethylamino)-6-isopropylamino-s-triazine; 4-amino-6-(t-butyl)-3-(methylthio)-1,2,4-triazine-5(4H)-one.

Diphenyl Ether Derivatives 2,4-dichloro-4'-nitrodiphenyl ether; 2,4,6-trichloro-4'-nitrodiphenyl ether; 2,4-dichloro-6-fluoro-4'-nitrodiphenyl ether; 3-methyl-4'-nitrodiphenyl ether; 3,5-dimethyl-5'-nitrodiphenyl ether; 2,4'-dinitro-4-(trifluoromethyl)diphenyl ether; 2,4-dichloro-3'-methoxy-4'-nitrodiphenyl ether; sodium 5-(2-chloro-4-(trifluoromethyl)phenoxy)-2-nitrobenzoate; 2-chloro-1-(3-ethoxy-4-nitrophenoxy)-4-(trifluoromethyl)benzene; 1-(carboethoxy)ethyl 5-[2-chloro-4-(trifluoromethyl)phenoxy]-2-nitrobenzoate; 5-[2-chloro-4-(trifluoromethyl)phenoxyl]-N-(methylsulphonyl)-2-nitrobenzamide.

Anilides 2-chloro-N-(2-ethyl-6-methylphenyl)-N-(2-methoxy-1-methylethyl)acetamide; 2-chloro-2',6'-diethyl-N-(2-propyloxyethyl)acetanilide; N-(3,4-dichlorophenyl)-propionamide; N-(3,4-dichlorophenyl)methacrylamide; N-(3-chloro-4-methylphenyl)-2-methylpentanamide; N-(3,4-dichlorophenyl)trimethylacetamide; N-(3,4-dichlorophenyl)-alpha,alpha-dimethylvaleramide; N-isopropyl-N-phenylchloroacetamide; N-n-butoxymethyl-N-(2,6-diethylphenyl)chloroacetamide; N-methoxymethyl-N-(2,6-diethylphenyl)chloroacetamide.

Oxyphenoxy Herbicides 2-(4-(2,4-dichlorophenoxy)phenoxy)methyl propionate; methyl 2-(4-(3-chloro-5-(trifluoromethyl)-2-pyridinyloxy)phenoxy)propanoate; butyl (R)-2-[4-[5-(trifluoromethyl)-2-pyridinyloxy]phenoxy]propionate; ethyl 2-[4-[(6-chloro-2-benzoxazolyl)oxy]phenoxy]-propanoate; butyl 2-[4-[[5-(trifluoromethyl)-2-pyridinyl]oxy]phenoxy]propionate; 2-[4-[(6-chloro-2-quinoxalinyl)oxy]phenoxy]propionic acid, ethyl ester.

Uracils 5-bromo-3-sec-butyl-6-methyluracil; 5-bromo-3-cyclohexyl-1,6-dimethyluracil; 3-cyclohexyl-5,6-trimethyleneuracil; 5-bromo-3-isopropyl-6-methyluracil; 3-tert-butyl-5-chloro-6-methyluracil.

Nitriles 2,6-dichlorobenzonitrile; diphenylacetonitrile; 3,5-dibromo-4-hydroxybenzonitrile; 3,5-diiodo-4-hydroxybenzonitrile.

Other Organic Herbicides 2-chloro-N,N-diallylacetamide; N-(1,1-dimethyl-2-propynyl)-3,5-dichlorobenzamide; maleic hydrazide; 3-amino-1,2,4-triazole; monosodium methanearsonate; disodium methanearsonate; N,N-dimethyl-alpha,alpha-diphenylacetamide; N-N-di(n-propyl)-2,6-dinitro-4-(trifluoromethyl)aniline; N,N-di(n-propyl)-2,6-dinitro-4-methylaniline; N,N-di(n-propyl)-2,6-dinitro-4-methylsulfonylaniline; O-(2,4-dichlorophenyl)-O-methyl isopropylphosphoramidothioate; 4-amino-3,5,6-trichloropicolinic acid; 2,3-dichloro-1,4-naphthoquinone; di(methoxythiocarbonyl)disulfide; 3-(1-methylethyl)-1H-2,1,3-benzothiadiazin-(4)3H-one-2,2-dioxide; 6,7-dihydrodipyridol[1,2-a:2',1'-c]pyrazidiium salts; 1,1'-dimethyl-4,4'-bipyridinium salts; 3,4,5,6-tetrahydro-3,5-dimethyl-2-thio-2H-1,3,5-thiadiazine; 2-[1-(ethoxyimino)butyl]-5-[s-(ethylthio)propyl]-3-hydroxy-2-cyclohexen-1-one; 2-(2-chlorophenyl)methyl-4,4-dimethyl-3-isoxazolidinone; N-(1-ethylpropyl)-3,4-dimethyl-2,6-dinitrobenzamide; 4-chloro-5-(methylamino)-2-(α,α,α-trifluoro-m-toluyl)-3-(2H)-pyridazinone; 2-(3,5-dichlorophenyl)-2-(2,2,2-trichloromethyl)oxirane; N,N-di(n-propyl)-2,6-dinitro-4-methylaniline; N,N-di(n-propyl)-2,6-dinitro-4-methylsulfonylaniline; O-(2,4-dichlorophenyl)-O-methyl isopropylphosphoramidothioate; 4-amino-3,5,6-trichloropicolinic acid; 2,3-dichloro-1,4-naphthoquinone; di(methoxythiocarbonyl)disulfide; 3-(1-methylethyl)-1H-2,1,3-benzothiadiazin-(4)3H-one-2,2-dioxide; 6,7-dihydrodipyridol[1,2-a:2',1'-c]pyrazidiium salts; 1,1'-dimethyl-4,4'-bipyridinium salts; 3,4,5,6-tetrahydro-3,5-dimethyl-2-thio-2H-1,3,5-thiadiazine; 2-[1-(ethoxyimino)butyl]-5-[s-(ethylthio)propyl]-3-hydroxy-2-cyclohexen-1-one; 2-(2-chlorophenyl)methyl-4,4-dimethyl-3-isoxazolidinone; N-(1-ethylpropyl)-3,4-dimethyl-2,6-dinitrobenzamide; 4-chloro-5-(methylamino)-2-(α,α,α-trifluoro-m-toluyl)-3-(2H)-pyridazinone; 2-(3,5-dichlorophenyl)-2-(2,2,2-trichloromethyl)oxirane.

I claim:

1. A compound of the formula

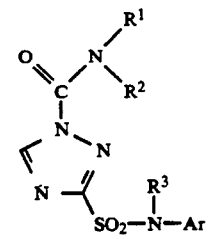

wherein
$R^1$ and $R^2$ are each independently selected from the group consisting of $(C_1-C_6)$alkyl, $(C_3-C_4)$alkenyl, $(C_3-C_4)$alkynyl, $(C_3-C_6)$cycloalkyl, $(C_3-C_6)$cycloalkyl$(C_1-C_2)$alkyl, $(C_5-C_6)$cycloalkenyl, $(C_5-C_6)$cycloalkenyl$(C_1-C_2)$alkyl, halo$(C_1-C_4)$alkyl, $(C_1-C_4)$alkoxy$(C_1-C_6)$alkyl and halo$(C_1-C_4)$alkoxy$(C_1-C_6)$alkyl, or $R^1$ and $R^2$ may together represent a $(C_4-C_5)$alkylene group or a $(C_4-C_5)$alkylene group substituted with up to two substitutents each independently selected from the group consisting of $(C_1-C_4)$alkyl, $(C_3-C_4)$alkenyl, $(C_3-C_4)$alkynyl, halo, halo$(C_1-C_4)$alkyl, $(C_1-C_4)$alkoxy$(C_1-C_4)$alkyl and halo$(C_1-C_4)$alkoxy$(C_1-C_4)$alkyl, so as to form a nitrogen-containing five or six membered cyclic ring with the nitrogen to which they attach, $R^3$ is hydrogen, $(C_1-C_6)$alkyl, $(C_3-C_4)$alkenyl, $(C_3-C_4)$alkynyl, $(C_3-C_6)$cycloalkyl, $(C_3-C_6)$cycloalkyl$(C_1-C_2)$alkyl, $(C_5-C_6)$cycloalkenyl, $(C_5-C_6)$cycloalkenyl$(C_1-C_2)$alkyl, halo$(C_1-C_4)$alkyl, $(C_1-C_4)$alkoxy$(C_1-C_6)$alkyl or halo$(C_1-C_4)$alkoxy$(C_1-C_6)$alkyl, Ar is a $(C_6-C_{10})$aryl group or a $(C_6-C_{10})$aryl group substituted with up to three substitutents each independently selected from the group consisting of $(C_1-C_6)$alkyl, $(C_2-C_4)$alkenyl, $(C_3-C_4)$alkynyl, halo$(C_1-C_4)$alkyl, $(C_1-C_4)$alkoxy, halo$(C_1-C_4)$alkoxy, $(C_1-C_4)$alkoxy$(C_1-C_6)$alkyl, halo$(C_1-C_4)$alkoxy$(C_1-C_6)$alkyl, cyano, nitro, $(C_1-C_4)$alkoxycarbonyl and $(C_1-C_4)$alkylthio, or the agronomically acceptable acid addition salts and metal complexes thereof.

2. The compound of claim 1 wherein
$R^1$ and $R^2$ are each independently selected from the group consisting of $(C_1-C_4)$alkyl, $(C_3-C_4)$alkenyl, $(C_3-C_4)$alkynyl and $(C_1-C_2)$alkoxy$(C_1-C_2)$alkyl, or $R^1$ and $R^2$ may together represent a $(C_4-C_5)$alkylene group so as to form a nitrogen-containing five or six-membered cyclic ring with the nitrogen to which they attach, $R^3$ is hydrogen, $(C_1-C_4)$alkyl, $(C_5-C_6)$cycloalkyl, halo$(C_1-C_2)$alkyl, $(C_1-C_2)$alkoxy$(C_1-C_2)$alkyl or halo$(C_1-C_2)$alkoxy$(C_1-C_2)$alkyl, and Ar is naphthyl or phenyl, or naphthyl or phenyl substituted with up to two substituents each independently selected from the group consisting of $(C_1-C_4)$alkyl, $(C_2-C_4)$alkenyl, $(C_3-C_4)$alkynyl, halo$(C_1-C_2)$alkyl, $(C_1-C_4)$alkoxy, halo$(C_1-C_2)$alkoxy, $(C_1-C_2)$alkoxy$(C_1-C_4)$alkyl and halo$(C_1-C_2)$alkoxy$(C_1-C_2)$alkyl.

3. The compound of claim 2 wherein
$R^1$ and $R^2$ are each independently selected from $(C_1-C_4)$alkyl or may together represent a $(C_4-C_5)$alkylene group so as to form a nitrogen-containing five or six membered cyclic ring with the nitrogen to which they attach,
$R^3$ is hydrogen, $(C_1-C_4)$alkyl, $(C_5-C_6)$cycloalkyl or $(C_1-C_2)$alkoxy$(C_1-C_2)$alkyl, and
Ar is phenyl or phenyl substituted with up to two substituents each independently selected from the group consisting of $(C_1-C_2)$alkyl, halo$(C_1-C_2)$alkyl, $(C_1-C_2)$alkoxy, halo$(C_1-C_2)$alkoxy and $(C_1-C_2)$alkoxy$(C_1-C_2)$alkyl.

4. The compound of claim 3 wherein
$R^1$ and $R^2$ are each independently selected from a $(C_1-C_4)$alkyl group,
$R^3$ is hydrogen, $(C_1-C_4)$alkyl or $(C_1-C_2)$alkoxy$(C_1-C_2)$alkyl, and
Ar is phenyl or phenyl substituted with up to two substituents each independently selected from methyl, ethyl, methoxy and ethoxy.

5. The compound of claim 4 wherein
$R^1$ and $R^2$ are each independently methyl or ethyl,
$R^3$ is hydrogen, methyl, isopropyl or methoxymethyl, and
Ar is phenyl, 2,6-dimethylphenyl or 2-methoxy-5-methylphenyl.

6. The compound of claim 5 which is
1-(N,N-diethylcarbamoyl)-3-(N-phenylsulfonamido)-1,2,4-triazole;
1-(N,N-diethylcarbamoyl)-3-[N-(2,6-dimethylphenyl)sulfonamido]-1,2,4-triazole;
1-(N,N-diethylcarbamoyl)-3-[N-(2,6-dimethylphenyl)-N-methylsulfonamido]-1,2,4-triazole;
1-(N,N-dimethylcarbamoyl)-3-(N-isopropyl-N-phenylsulfonamido)-1,2,4-triazole;
1-(N,N-diethylcarbamoyl)-3-[N-(2-methoxy-5-methylphenyl)sulfonamido]-1,2,4-triazole;
1-(N,N-diethylcarbamoyl)-3-(N-isopropyl-N-phenylsulfonamido)-1,2,4-triazole; or
1-(N,N-diethylcarbamoyl)-3-[N-methoxymethyl-N-(2-methoxy-5-methylphenyl)sulfonamido]-1,2,4-triazole.

7. A herbicidal composition which comprises an agronomically acceptable carrier and a herbicidally effective amount of the compound of claim 1.

8. A herbicidal composition which comprises an agronomically acceptable carrier and a herbicidally effective amount of the compound of claim 2.

9. A herbicidal composition which comprises an agronomically acceptable carrier and a herbicidally effective amount of the compound of claim 4.

10. A herbicidal composition which comprises an agronomically acceptable carrier and a herbicidally effective amount of the compound of claim 6.

11. A method for controlling unwanted plants which comprises applying to the plant or growth medium of the plants a herbicidally effective amount of the compound of claim 1.

12. A method for controlling unwanted plants which comprises applying to the plant or growth medium of the plants a herbicidally effective amount of the compound of claim 2.

13. A method for controlling unwanted plants which comprises applying to the plant or growth medium of the plants a herbicidally effective amount of the compound of claim 4.

14. A method for controlling unwanted plants which comprises applying to the plant or growth medium of the plants a herbicidally effective amount of the compound of claim 6.

* * * * *